(12) United States Patent
Razavi et al.

(10) Patent No.: US 9,237,936 B2
(45) Date of Patent: Jan. 19, 2016

(54) SYSTEM AND METHOD FOR INTEGRATING CANDIDATE IMPLANT LOCATION TEST RESULTS WITH REAL-TIME TISSUE IMAGES FOR USE WITH IMPLANTABLE DEVICE LEADS

(71) Applicant: Pacesetter, Inc., Sunnyvale, CA (US)

(72) Inventors: Hoda Razavi, San Jose, CA (US); Edith Arnold, San Francisco, CA (US); Fujian Qu, San Jose, CA (US); Yelena Nabutovsky, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/940,741

(22) Filed: Jul. 12, 2013

(65) Prior Publication Data
US 2015/0018907 A1 Jan. 15, 2015

(51) Int. Cl.
*A61B 19/00* (2006.01)
*A61N 1/05* (2006.01)

(52) U.S. Cl.
CPC ............. *A61B 19/5244* (2013.01); *A61B 19/56* (2013.01); *A61B 2019/524* (2013.01); *A61B 2019/5238* (2013.01); *A61B 2019/5251* (2013.01); *A61B 2019/5276* (2013.01); *A61N 1/056* (2013.01)

(58) Field of Classification Search
CPC ............................. A61B 5/684; A61B 5/6841
USPC ........................................................ 607/116
See application file for complete search history.

(56) References Cited

U.S. PATENT DOCUMENTS

| 6,925,334 | B1 | 8/2005 | Salys |
| 6,968,237 | B2 | 11/2005 | Doan et al. |
| 7,386,339 | B2 | 6/2008 | Strommer et al. |
| 7,590,447 | B2 | 9/2009 | Dingman et al. |
| 7,881,769 | B2 | 2/2011 | Sobe |
| 7,890,190 | B1 | 2/2011 | Salys et al. |
| 7,920,920 | B1 | 4/2011 | Williamson |
| 8,055,327 | B2 | 11/2011 | Stommer et al. |
| 8,131,344 | B2 | 3/2012 | Strommer et al. |
| 8,238,625 | B2 | 8/2012 | Strommer et al. |
| 8,285,377 | B2 | 10/2012 | Rosenberg et al. |
| 8,326,419 | B2 | 12/2012 | Rosenberg et al. |
| 8,442,618 | B2 | 5/2013 | Strommer et al. |
| 2004/0097804 | A1 | 5/2004 | Sobe |
| 2008/0183071 | A1 | 7/2008 | Strommer et al. |
| 2010/0268059 | A1 | 10/2010 | Ryu et al. |
| 2011/0028894 | A1 | 2/2011 | Foley et al. |

(Continued)

*Primary Examiner* — Joseph Dietrich
(74) *Attorney, Agent, or Firm* — Theresa A. Raymer

(57) ABSTRACT

Patient tissues are imaged using, e.g., a real-time fluoroscopic imaging system, along with a lead system being implanted. Parameters representative of lead placement efficacy—such as capture thresholds, phrenic nerve stimulation thresholds, impedance values or screw-in tip mechanical resistance values—are measured at candidate implant locations. Localization parameters identifying the candidate implant locations are also measured. In one example, a display is generated substantially in real-time showing: images of the tissues of the patient and the lead system being implanted; candidate locations of the electrodes; and parameters representative of lead placement efficacy at the candidate locations. In this manner, the implanting clinician can readily view capture thresholds and other helpful parameters at various candidate locations along with actual real-time images of the tissues of the patient and the lead system being implanted. Recorded images can also be displayed and, in some examples, multiple images can be superimposed over one another.

27 Claims, 8 Drawing Sheets

(56) References Cited

U.S. PATENT DOCUMENTS

| | | |
|---|---|---|
| 2011/0054560 A1 | 3/2011 | Rosenberg et al. |
| 2011/0144510 A1 | 6/2011 | Ryu et al. |
| 2011/0160792 A1* | 6/2011 | Fishel .......................... 607/27 |
| 2011/0213260 A1 | 9/2011 | Keel et al. |
| 2012/0016253 A1 | 1/2012 | Koh et al. |
| 2012/0078080 A1 | 3/2012 | Foley et al. |
| 2012/0184955 A1 | 7/2012 | Pivotto et al. |
| 2014/0176944 A1* | 6/2014 | Addison et al. ............... 356/400 |

* cited by examiner

SYSTEM AND METHOD FOR INTEGRATING CANDIDATE IMPLANT LOCATION TEST RESULTS WITH REAL-TIME TISSUE IMAGES FOR USE WITH IMPLANTABLE DEVICE LEADS

FIELD OF THE INVENTION

Aspects of the invention relate to device programmers for use with implantable medical devices and to medical positioning and display systems for use during implantation of the lead systems of such medical devices.

BACKGROUND OF THE INVENTION

Implantation of lead systems for pacemakers or other implantable medical devices often requires the testing of candidate lead locations for parameters such as myocardial capture thresholds, phrenic nerve stimulation thresholds, electrical impedance values, and the like. Herein, these and other related parameters are referred to as "lead implant efficacy parameters" since the parameters pertain to the efficacy or suitability of particular lead implant locations. In practice, the implanting clinician often tests a number of candidate implant locations while observing the location of the lead within the patient using fluoroscopic images or the like. At a particular candidate location, the clinician typically employs a device programmer or pacing system analyzer (PSA) to perform various suitability tests, such as capture threshold tests to ensure the capture threshold at the candidate location is not too high (which would necessitate high stimulation pulse amplitudes), phrenic nerve stimulation (PNS) tests to ensure that the PNS threshold is not too low (which might otherwise result in adverse diaphragmatic stimulation triggered by the stimulation pulses), and impedance measurements to ensure that impedance is not too high (which might cause undue current drain from the device battery) or too low (which might indicate lack of tissue contact).

During the lead implant procedure, if a candidate location is unsatisfactory, the lead is maneuvered to different location and the tests are repeated. The testing procedure usually needs to be repeated for each lead to be implanted and, in some cases, for multiple electrodes of a particular lead. In the case of state-of-the-art implantable cardiac rhythm management devices (CRMDs) such as implantable cardioverter-defibrillators (ICDs), cardiac resynchronization devices (CRTs) and the like, the lead systems may include a bipolar right atrial (RA) lead, a bipolar right ventricular (RV) lead, and a multi-polar left ventricular (LV) lead implanted via the coronary sinus (CS). For such systems, it is important that the various tests be performed as efficiently as possible and that particular candidate locations are tested only once. However, the two-dimensionality of conventional fluoroscopic images can make it difficult for the clinician to know exactly which locations have already been tested. As such, the same location may be inadvertently tested multiple times with the same capture threshold outcomes. This can be especially problematic if an active fixation lead needs to be inserted into cardiac tissue with each test, damaging the tissue at the site. Multiple fixations around the same area can be life-threatening, especially within the thin-walled chambers of the heart such as the RA and RV. Still further, some implant locations might have residual scar tissue due to myocardial infarction or other conditions, which can render the location undesirable for implantation, a problem not readily discernible from standard fluoroscopic images.

Some of these concerns are addressed by systems such as the one described in U.S. Pat. No. 8,285,377 to Rosenberg et al., entitled "Pacing, Sensing and Other Parameter Maps based on Localization System Data." Various exemplary techniques described therein pertain to multi-dimensional mapping of one or more parameters germane to cardiac pacing therapy, which exploit the EnSite™ and NavX™ cardiac mapping and navigation systems provided by the assignee of the present application. For example, during an intraoperative procedure, a clinician may maneuver a catheter to various locations in one or more chambers or vessels of the heart and deliver energy at the various locations using electrodes of the catheter. Sensing equipment senses electrical signals responsive to the delivered energy and, in turn, a 3-D mapping application associates the signals with the various locations. In a specific example, the mapping application generates a capture threshold map for use by a clinician to locate electrodes chronically. Phrenic nerve stimulation can also be assessed, as well as pacing impedance. Illustrative displays generated using the techniques of Rosenberg et al. exploit 3-D graphical maps of heart chambers and lumens generated by the EnSite™ and NavX™ systems or instead use preprogrammed and scalable graphical models of the human heart.

Although the systems and methods of Rosenberg et al. are advantageous, further improvement is warranted. For example, whereas the techniques of Rosenberg et al. provide for the display of certain lead implant efficacy parameters along with 3-D graphical maps or scalable graphical models of the heart, it would be desirable to provide a system that instead displays lead implant efficacy parameters along with fluoroscopic (or similar) images of the actual tissues of the patient. Moreover, as currently implemented with EnSite™ systems, the leads are not directly visible, as in fluoroscopic images. Still further, it would desirable to provide a system that addresses concerns over lead fixation into scar tissue or multiple insertions of active fixation leads into thin-walled chambers. Accordingly, it would be desirable to provide improved systems and procedures to address these or other issues, and it is to that end that aspects of the present invention are directed.

SUMMARY OF THE INVENTION

In an exemplary embodiment, a method is provided for use with an implantable medical lead system for implant within a patient. Briefly, tissues of the patient are imaged along with portions of the lead system being implanted using, e.g., a real-time fluoroscopic imaging system. One or more parameters representative of lead placement efficacy—such as myocardial capture thresholds. PNS thresholds, electrical impedance values or screw-in tip mechanical resistance values—are measured at candidate implant locations within the tissues of the patient using repositionable electrodes of the lead system. Localization parameters identifying the candidate implant locations are also measured. A display is generated showing: images of the tissues of the patient and at least a portion of the lead system being implanted; the candidate locations of the repositionable electrodes; and parameters representative of lead placement efficacy at the candidate locations such as capture thresholds or the mechanical resistance values. In some examples, the efficacy values are color-coded without showing actual numerical values. Moreover, thresholds may be set such that only "acceptable" sites based on the thresholds are highlighted. That is, thresholds can be used to facilitate the visualization of the lead parameters as a way to avoid cluttering of the image. In examples where sensor icons are displayed, the icons may also change color to indicate acceptable or non-acceptable lead parameters to thereby aid the visualization of the localization parameters on the images. Using these or other visualization techniques, the implanting clinician can readily view capture thresholds and/or icons and other helpful parameters at various candidate implant locations along with actual images of the tissues of the patient and the lead system being implanted. Preferably, real-time or near real-time images are used, although recorded images can also be displayed and, in some examples, multiple images can be superimposed over one another, some in real-time and some recorded.

In an illustrative implementation, the imaging system exploits fluoroscopic imaging, computer aided tomography (CT), ultrasonography or other suitable real-time or near real-time imaging techniques that produce actual images of tissues of the patient, Leads are manually or robotically inserted into the patient to position electrodes—such as the tip electrode of an RV lead of a pacemaker, CRT or ICD—at candidate locations within the heart of the patient while the heart and the lead system are being imaged. A device programmer or PSA then measures parameters representative of lead placement efficacy at the candidate locations. For example, the programmer may perform one or more of: capture tests to assess the myocardial capture threshold; PNS tests to assess phrenic nerve stimulation and to further determine whether a PNS threshold is too low at the candidate location; impedance tests to measure electrical impedance of the lead; and mechanical resistance tests to assess the resistance to active fixation based, e.g., on the torque required to screw-in the tip of the lead.

Concurrently, the illustrative system uses an MPS such as the MediGuide™ system (owned by the assignee of the present application) to measure or detect localization parameters identifying the position and orientation of the electrodes and corresponding candidate implant locations, where the localization parameters are specified relative to a reference coordinate system for conversion to 3-D location coordinates. If active fixation leads are used, the system determines a safety distance around each candidate implant location based on a pre-programmed minimum safe distance or other factors. The minimum safe distance specifies a minimum distance from a prior active fixation site sufficient so that a new active fixation will not result in undue damage to the heart tissue (as might otherwise occur if two active fixation locations are too close together, especially within thin-walled chambers such as the RA.) The MPS system then selectively generates a real-time display showing the heart of the patient and surrounding vasculature along with the current candidate implant location and any previously analyzed candidate locations (via suitable icons or landmarks or colors.) The display further shows various lead implant efficacy parameters such as: capture thresholds at each tested candidate location; PNS thresholds at each tested candidate location (or warning indicators if PNS thresholds are too low compared to corresponding capture thresholds); minimum safe distances around active fixation candidate locations; electrical impedance values measured for each candidate location; and warning indicators if the mechanical resistance measured at a candidate location indicates significant scar tissue (as may be determined by comparing measured mechanical resistance values to pre-determined thresholds indicative of excessive scar tissue.)

Exemplary system and method embodiments are described herein primarily with reference to the implantation of lead systems of CRMDs, but the general principles of the invention are applicable to other implantable medical devices and lead systems, such as leads employed for stimulating other organs.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Systems and Methods

Figure 1:
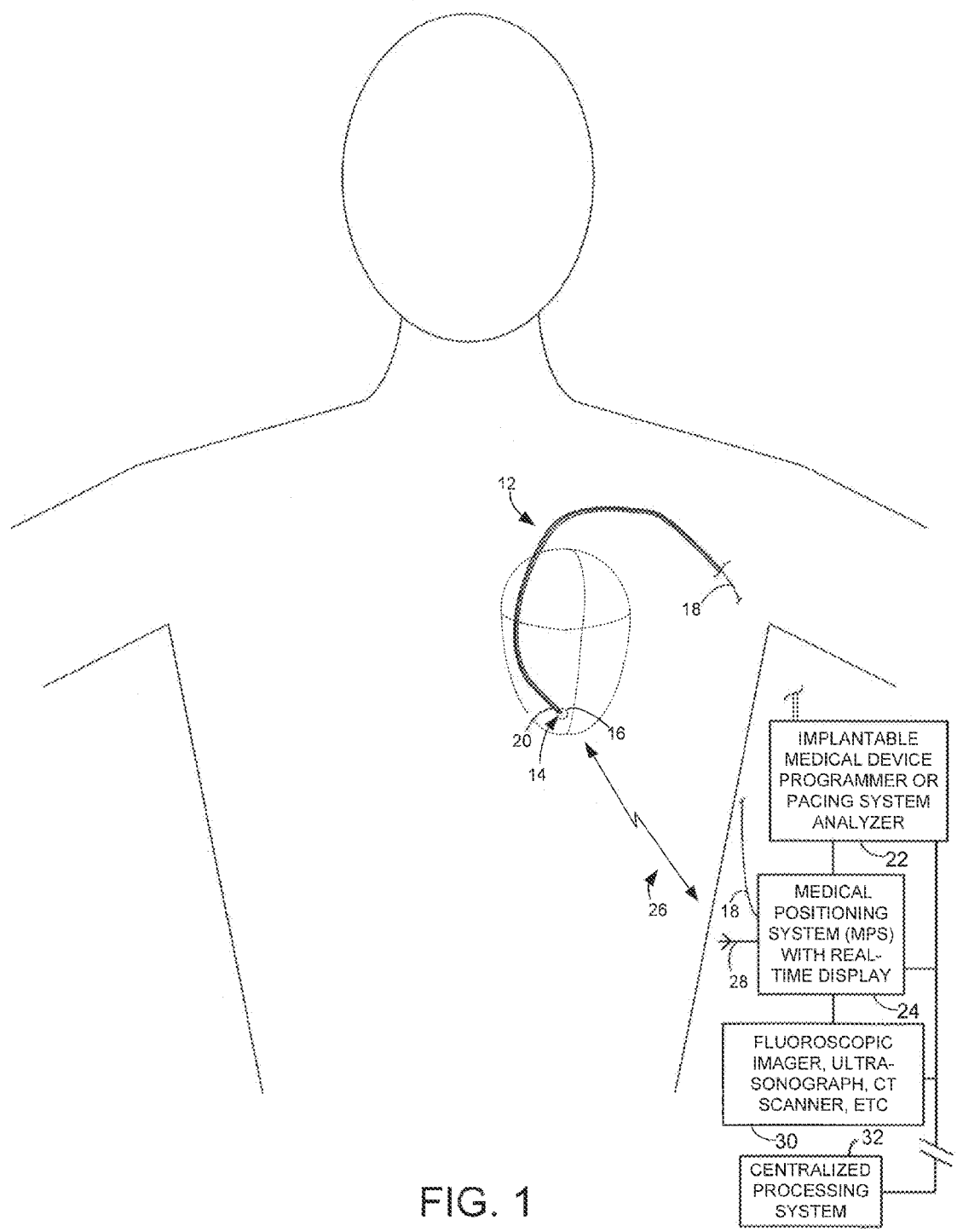
FIG. 1 illustrates pertinent components of a system for imaging an implantable medical lead during implant and for integrating lead localization information with implant location efficacy parameters such as capture thresholds.

FIG. 1 provides a stylized illustration of pertinent portions of an implantable medical lead 12 having an active fixation tip electrode 14 for implant into the RV of the heart of a patient, with the lead shown positioned at a candidate implant location 16. (Note that, for clarity and simplicity, not all of the features of the RV lead are shown, such as its ring electrode or its shocking coil electrode or any physiological sensors that might be mounted to the lead. Also, note that other leads can additionally or alternatively be implanted, such as RA or LV/CS leads. See FIG. 8, discussed below, for a more complete illustration of an exemplary lead system following implant.) FIG. 1 also illustrates a portion of a stylet or guidewire 18 removably inserted within lead 12 and having an electromagnetic field detector 20 for use in obtaining localization information indicating the location and orientation of the tip of the lead. (Note that not all implantation components or tools are necessarily shown, such as additional guidewires, sheaths, etc., which might be needed or exploited during the implantation procedure.) Once the tip of the RV lead is positioned or installed at a candidate location, a device programmer or PSA system 22 obtains, measures or otherwise detects various lead implant efficacy parameters—such as capture thresholds, PNS thresholds, electrical impedance values or screw-in tip mechanical resistance values—using lead 12 and its various electrodes or sensors. Exemplary techniques for obtaining these parameters are discussed below. In one example, programmer 22 includes, or is connected to, a Merlin™ programmer system provided by the assignee of the present application.

While the lead is being inserted into the RV, an MPS 24 tracks the location of the tip of the lead by applying electromagnetic signals 26 via an antenna 28. The electromagnetic field detector 20 responds to the signals, thereby allowing the MPS to localize the tip of the lead in 3D relative to a predetermined reference coordinate system. In one example, the MPS includes, or is connected to, a MediGuide™ system provided by the assignee of the present application. The overall system also includes a real-time tissue imaging system 30 such as a fluoroscopic imager, ultrasonograph (i.e. ultrasound), CT scanner, or the like for obtaining real time images of the tissues of the patient (and the lead being implanted) for feeding into a display system of the MPS. Other suitable imaging systems that can be used might exploit X-rays; nuclear magnetic resonance (NMR); radioactive imaging; and/or thermography. Depending upon the particular implementation of the overall system, image detector 30 may be a component of MPS system 24, or vice versa, and either or both might be integrated with programmer 22. The various components may also be connected to a centralized computing system 32, such as the HouseCall™ system or the Merlin@home/Merlin.Net systems of St. Jude Medical, which can store pertinent patient data for subsequent retrieval. As can be appreciated, a wide range of implementation options is available.

In use, during lead implant, the clinician or physician maneuvers the tip of the lead to various candidate locations within the heart of the patient while observing the real-time display. The various lead implant efficacy parameters such as capture thresholds, etc, are superimposed on the display so the clinician or physician can readily view the capture thresholds and other helpful parameters at various candidate implant locations along with actual real-time images of the tissues of the patient and the lead system being implanted. That is, in some examples capture threshold information is displayed near the test site for at least two fluoroscopic views such that upon the identification of a preferred or optimal implant site, the lead can be maneuvered back to that preferred or optimal location. As already noted, real-time or near real-time images are preferably used, although recorded images can also be displayed and, in some examples, multiple images can be superimposed over one another, some in real-time and some recorded, Pertinent details of exemplary implementations are set forth below. Note also that, although an exemplary endocardial lead is shown in FIG. 1, other intravenous, pericardial, subcutaneous or "leadless" pacing devices may additionally or alternatively be used.

Figure 2:
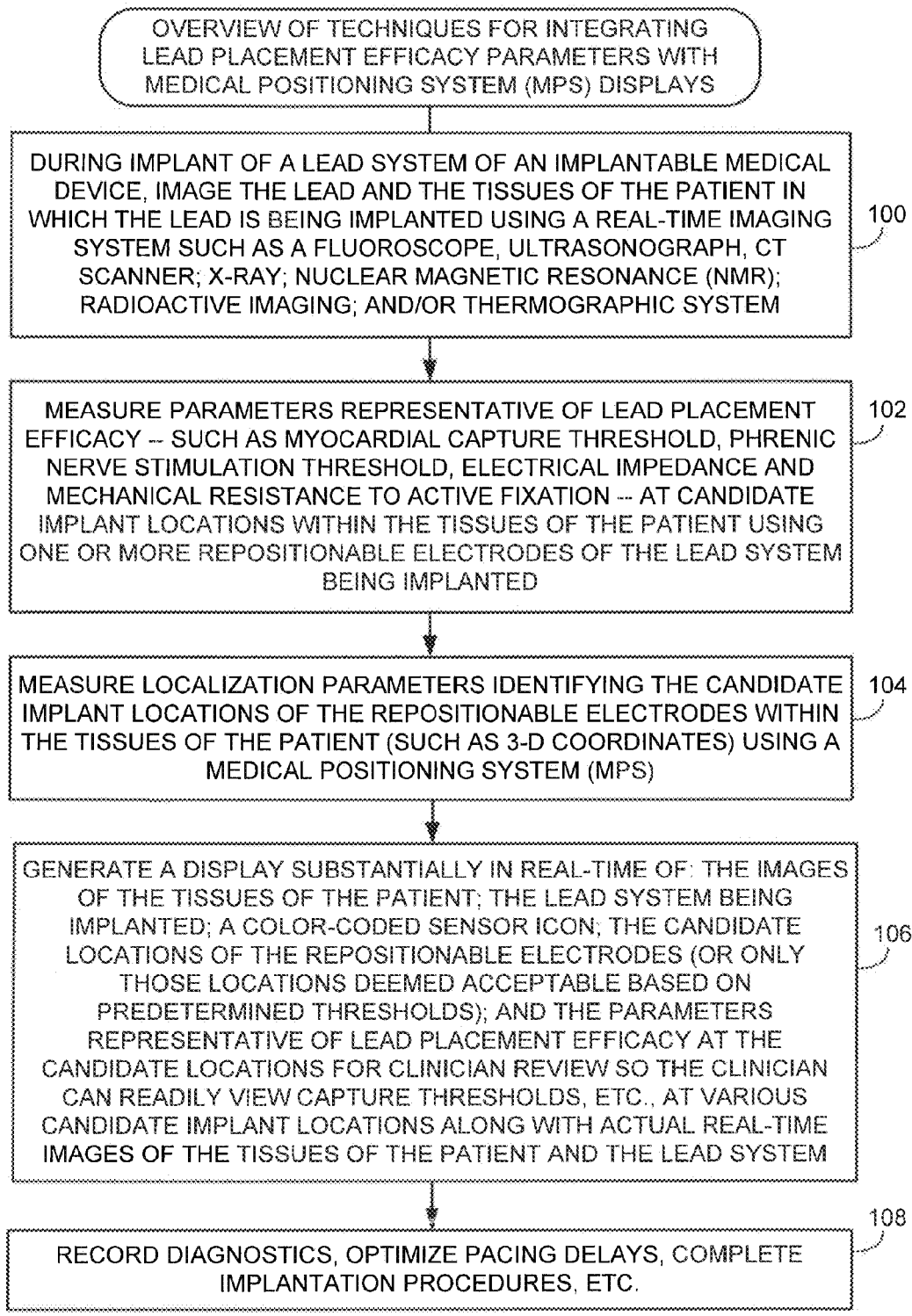
FIG. 2 provides an overview of an exemplary technique for integrating real-time tissue images with implant location efficacy parameters performed by the system of FIG. 1.

FIG. 2 broadly summarizes techniques exploited by the system of FIG. 1 (or other suitably-equipped systems) for integrating lead placement efficacy parameters with real-time MPS tissue displays. Beginning at step 100, during implant of a lead system of an implantable medical device, the imaging components of the integrated system generate images of the lead and the tissues of the patient in which the lead is being implanted using a real-time imaging system or scanner such as a fluoroscopic, ultrasonographic or CT system. As noted, other suitable imaging systems that can be used might exploit X-rays, NMR; and/or thermography. At step 102, the device programmer components of the integrated system measure parameters representative of lead placement efficacy such as myocardial capture threshold, phrenic nerve stimulation threshold, electrical impedance and mechanical resistance to active fixation at candidate implant locations within the tissues of the patient using one or more repositionable electrodes of the lead system being implanted. At 104, the lead localization components of the integrated system measure localization parameters for identifying the candidate implant locations of the repositionable electrodes within the tissues of the patient (such as 3-D coordinates.) At step 106, the display components of the integrated system generate a display substantially in real-time of: the images of the tissues of the patient; the lead system being implanted; a color-coded sensor icon (such as a MediGuide™ sensor icon that changes color to indicate acceptable or non-acceptable lead parameter); the candidate locations of the repositionable electrodes (or only those locations deemed acceptable based on predetermined thresholds); and the parameters representative of lead placement efficacy at the candidate locations for clinician review so the clinician can readily view capture thresholds, etc., at various candidate implant locations along with actual real-time images of the tissues of the patient and the lead system. At step 108, components of the integrated system record diagnostics, optimize pacing delays or perform other suitable implant or post-implant functions that the various components of the system are equipped to perform. Note that, although shown sequentially, it should be understood that (where appropriate) the various steps could be performed concurrently or in a different order than shown in FIG. 2. Ultimately, the lead implant procedures are completed and then the pacemaker, CRT, ICD or other implantable medical device is implanted, connected to the leads and tested. One or more follow-up sessions can be used to adjust control parameters of the implantable medical device, if needed.

Hence, FIGS. 1 and 2 provide an overview of systems and methods for integrating lead placement efficacy parameters with real-time MPS tissue displays. These techniques will now be described in more detail with reference to various exemplary embodiments.

Illustrative Systems and Methods

Figure 3:
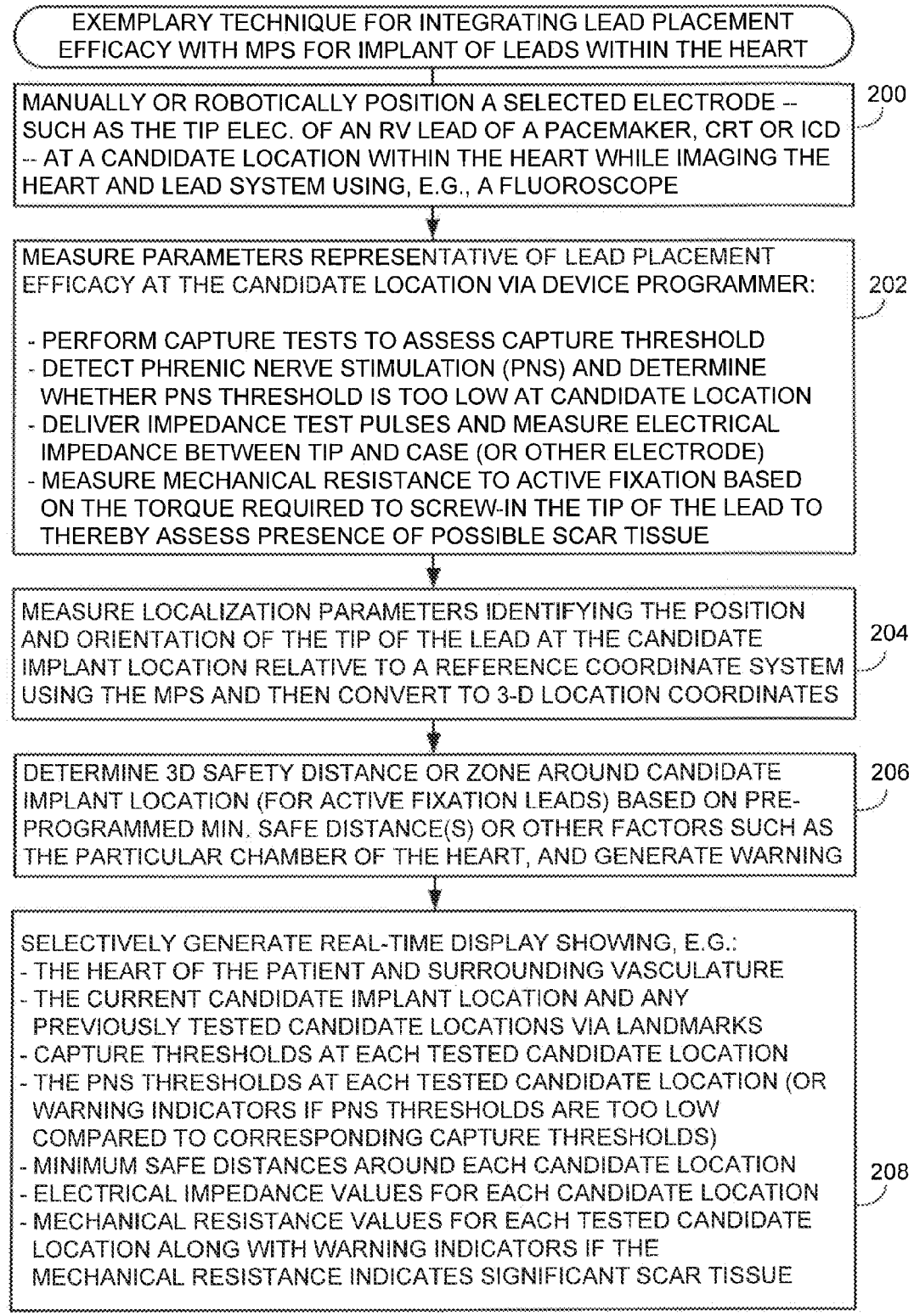
FIG. 3 illustrates an exemplary technique for integrating real-time tissue images with implant location efficacy parameters in accordance with the general technique of FIG. 2.

FIG. 3 illustrates an exemplary technique exploited by the integrated system of FIG. 1, Beginning at step 200, during implant of a lead system of an implantable medical device, the clinician manually or robotically positions a selected electrode—such as the tip electrode of the RV lead of a pacemaker, CRT or ICD—at a candidate location within the heart while imaging the heart and the lead system using, e.g., a fluoroscope. See, for example, techniques described in U.S. Pat. No. 8,055,327 to Strommer et al, entitled "Automatic Guidewire Maneuvering System and Method" and U.S. Pat. No. 8,442,618 also to Strommer et al., entitled "Method and System for Delivering a Medical Device to a Selected Position within a Lumen." See, also, MPS-based lead implantation procedures described in U.S. Pat. No. 7,881,769 to Sobe, entitled "Method and System for Mounting an MPS Sensor on a Catheter." Imagining systems are discussed, for example, in U.S. Patent Application 2008/0183071 of Strommer et al., entitled "System and Method for Superimposing a Representation of the Tip of a Catheter on an Image Acquired by a Moving Imager."

At step 202, the integrated system measures parameters representative of lead placement efficacy at the candidate location via a device programmer. As noted, the system may perform capture tests to assess myocardial capture thresholds. Capture is discussed, e.g., in U.S. Pat. No. 7,920,920 to Williamson, entitled "Algorithm for Capture Detection." Also at step 202, the system may detect a PNS threshold and determine whether PNS threshold is too low at the candidate location by, for example, determining whether a lowest amplitude pacing pulse sufficient to achieve capture (with a safety margin) would nevertheless still trigger PNS. PNS is discussed, for example, in U.S. Patent Application 2011/0213260 of Keel et al., entitled "CRT Lead Placement based on Optimal Branch Selection and Optimal Site Selection."

Also at step 202, the system may deliver impedance test pulses and measure electrical impedance between the electrode being implanted and another electrode. A particularly effective tri-phasic impedance detection pulse for use in measuring impedance is described in U.S. patent application Ser. No. 11/558,194 of Panescu et al., filed Nov. 9, 2006, entitled "Closed-Loop Adaptive Adjustment of Pacing Therapy based on Cardiogenic Impedance Signals Detected by an Implantable Medical Device." See, also, techniques described in U.S. patent application Ser. No. 13/007,424 of Gutfinger et al., filed Jan. 14, 2011, entitled "Systems and Methods for Exploiting Near-Field Impedance and Admittance for use with Implantable Medical Devices" and U.S. patent application Ser. No. 12/853,130 of Gutfinger at al., filed Aug. 9, 2010, entitled "Near Field-Based Systems and Methods for Assessing Impedance and Admittance for use with an Implantable Medical Device."

At step 202, the system may also measure parameters representative of mechanical resistance to active fixation based, e.g., on the torque required to screw-in the tip of the lead to thereby assess the presence of possible scar tissue. That is, substrate characterization can be based on the mechanical resistance of the screw-in lead such that higher resistance would indicate a larger degree of scarred tissue. Hence, at each candidate site, the system can assess the mechanical properties of the cardiac tissue being tested and the characterization of the substrate at each site can thereby guide the implanting physician to place the lead away from scar tissue. A predetermined threshold of tissue resistance may be exploited, below which the cardiac tissue is considered healthy and above which some is deemed to scarring exist. Torque measurements involving catheters are discussed, e.g., in U.S. Patent Application 2012/0184955 of Pivotto et al., entitled "Remotely Controlled Catheter Insertion System with Automatic Control System." The measured torque may then be compared against a predetermined threshold representative of an excess of scar tissue with suitable warnings generated to alert the clinician if scar tissue is present or excessive. Suitable thresholds may be determined in advance without undue experimentation by, for example, measuring the amount of mechanical resistance required to insert test leads into various samples of myocardial tissue having differing amounts of scar tissue in a laboratory setting. In vivo experiments may also be necessary or appropriate to determine such thresholds after appropriate bench-top testing.

At step 204, the integrated system measures localization parameters identifying the position and orientation of the tip of the lead at the candidate implant location relative to a reference coordinate system using the MPS and then converts to 3-D location coordinates, if needed. See, e.g. U.S. Pat. No. 8,131,344 to Strommer et al., entitled "Method and System for Registering a Medical Situation associated with a First Coordinate System, in a Second Coordinate System using an MPS System." At step 206, the system determines a safety distance around each candidate implant location (for active fixation leads) based on pre-programmed minimum safe distances or other factors such as the particular chamber of the heart. In this regard, one or more safety distances can be programmed such that each test location is at least that distance away from all other previous test locations. This helps ensure that active fixations are not being made too close to one another to introduce cardiac tissue perforation. In some examples, the safety zone is calculated in 3D and the appropriate zone for subsequent projection onto 2D views. The system may also provide an auditory and/or visual feedback system such as an alert that can sound if the lead is approaching the safety zone, warning the physician to keep away from an already-tested site.

At step 208, the integrated system then selectively generates real-time displays showing one or more of: the heart of the patient and surrounding vasculature; the current candidate implant location and any previously tested candidate locations via landmarks; capture thresholds at each tested candidate location; the PNS thresholds at each tested candidate location (or warning indicators if PNS thresholds are too low compared to corresponding capture thresholds); minimum safe distances around each candidate location; electrical impedance values for each candidate location (or warning indicators if the measured impedance is too high); mechanical resistance values for each tested candidate location along with warning indicators if the mechanical resistance indicates significant scar tissue. As can be appreciated, there are various different embodiments for the placement of capture threshold markers on the screen. In particular, in one embodiment, the MPS system automatically receives this information from the device programmer or PSA and automatically displays the information as soon as threshold testing (or other tests) are completed. The implanting physician or an assistant can also press a foot pedal or click on the system to display the information. In other embodiment, the system operator places a landmark with capture threshold values incorporated after the threshold testing is completed.

Figure 4:
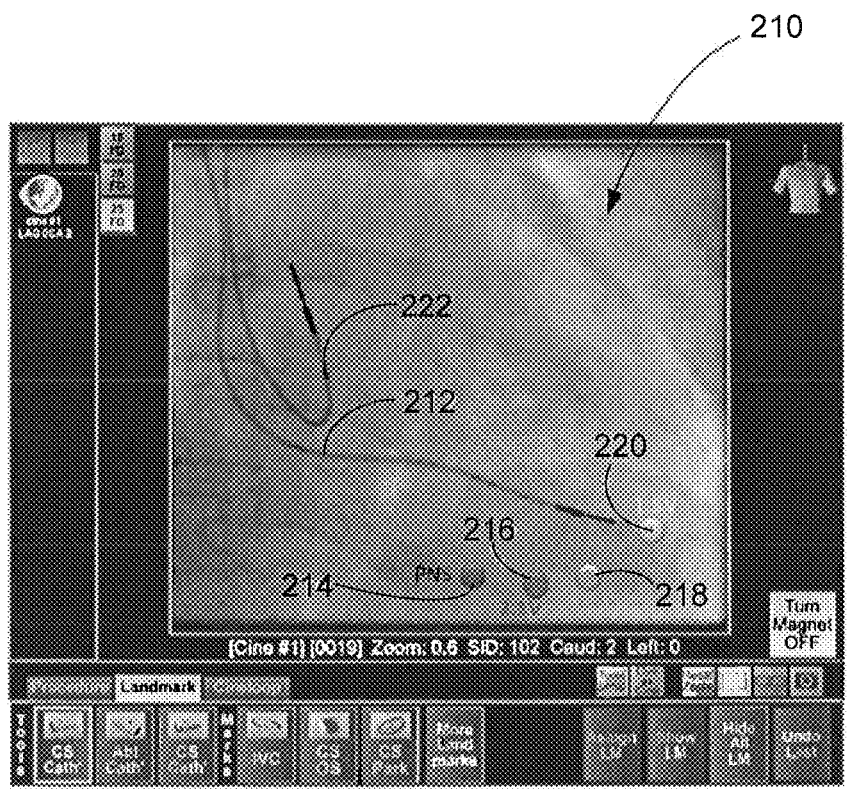
FIG. 4 provides an exemplary display of tissue images and implant location efficacy parameters generated using the exemplary technique of FIG. 3.

FIG. 4 provides an exemplary display that may be generated at step 208 of FIG. 3, wherein PNS and capture threshold tests have been performed for an RV lead. In this example, a fluoroscopic display 210 of tissues is presented, which shows the current location of an RV lead 212 being implanted. Four candidate tip locations have been tested, including the current location of the RV lead. Hence, the display shows four icons. At a first candidate location or site, the PNS threshold was found to be too low and so an indicator icon 214 is provided (preferably in red) that identifies the candidate site and provides a text label of "PNS" to alert the clinician to the risk of PNS if the tip of the RV lead were chronically implanted at that site. A second candidate location was found to have an acceptable PNS threshold with a capture threshold of 2.1 V. Accordingly, an indicator 216 is provided (preferably in green) that identifies the candidate site and provides at text annotation of the capture threshold. A third candidate location was found to have a capture threshold of 1.8 V and an indicator 218 is provided (preferably in a lighter shade of green) that identifies the site and provides a text annotation of the particular capture threshold. A fourth candidate location was found to have a capture threshold of 1.5 V and an indicator 220 is provided (preferably in a still lighter shade of green) that identifies the candidate site and provides text denoting the particular capture threshold. Hence, in this example, the lower the capture threshold, the lighter the shade of green, thus providing the clinician with conveniently color-coded icons (in addition to, or instead of, textual or numerical values.) As noted above, thresholds may be set such that only "acceptable" sites based on the thresholds are highlighted. That is, thresholds can be used to facilitate the visualization of the lead parameters to thereby avoid cluttering of the image. In examples where a MediGuide™ sensor icon is displayed, the sensor icon itself may also change color to indicate acceptable or non-acceptable lead parameter to thereby aid the visualizations of the localization parameters on the images. As can be seen in the particular example of FIG. 4, the display also presents other textual information pertaining to the image along with various commands for manipulating the image, such as to add additional landmarks or other icons or to zoom in on parts of the image, all under the control of the clinician. Further information regarding display systems of the type shown in FIG. 4 may be found in the patents and patent applications initially assigned to MediGuide Ltd., particularly in U.S. Patent Application 2008/0183071, cited above. Note that the exemplary display of FIG. 4 also shows an RA lead 222, which has not yet been tested for PNS or capture thresholds and hence no icons or landmarks are displayed for the RA lead. Also note that, in other examples, the system might display superimposed images of the lead at its various tested locations (rather than just icons showing the results of those tests.)

Figure 5:
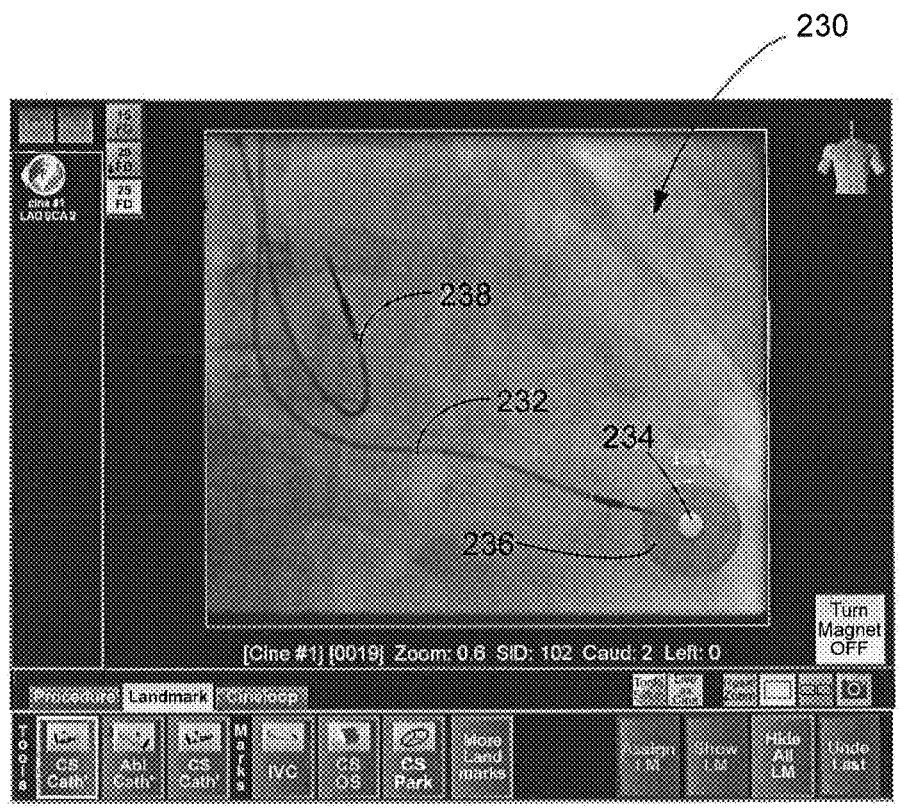
FIG. 5 provides another exemplary display of tissue images and implant efficacy parameters generated using the exemplary technique of FIG. 3.

FIG. 5 provides another exemplary display that may be generated at step 208 of FIG. 3, wherein capture threshold tests have been performed for an RV lead and a 3D safety zone has been determined. In this example, a fluoroscopic display 230 of patient tissues is presented, which provides a single image of an RV lead 232 being implanted at a candidate location in the RV. At the candidate location, an indicator 234 is displayed (preferably in green) that identifies the candidate site and provides a text annotation of the capture threshold, which is 1.5 V. A larger icon (preferably in red) shows the 3D safety zone around the site, as may be determined at step 206 of FIG. 3. The clinician is thereby alerted not to attempt another active fixation within that zone. The display of FIG. 5 also shows an RA lead 238, which has not yet been tested and hence no icons or landmarks are displayed for the RA lead. Again, the display also presents other textual information pertaining to the image and various commands for manipulating the image under the control of the clinician.

Figure 6:
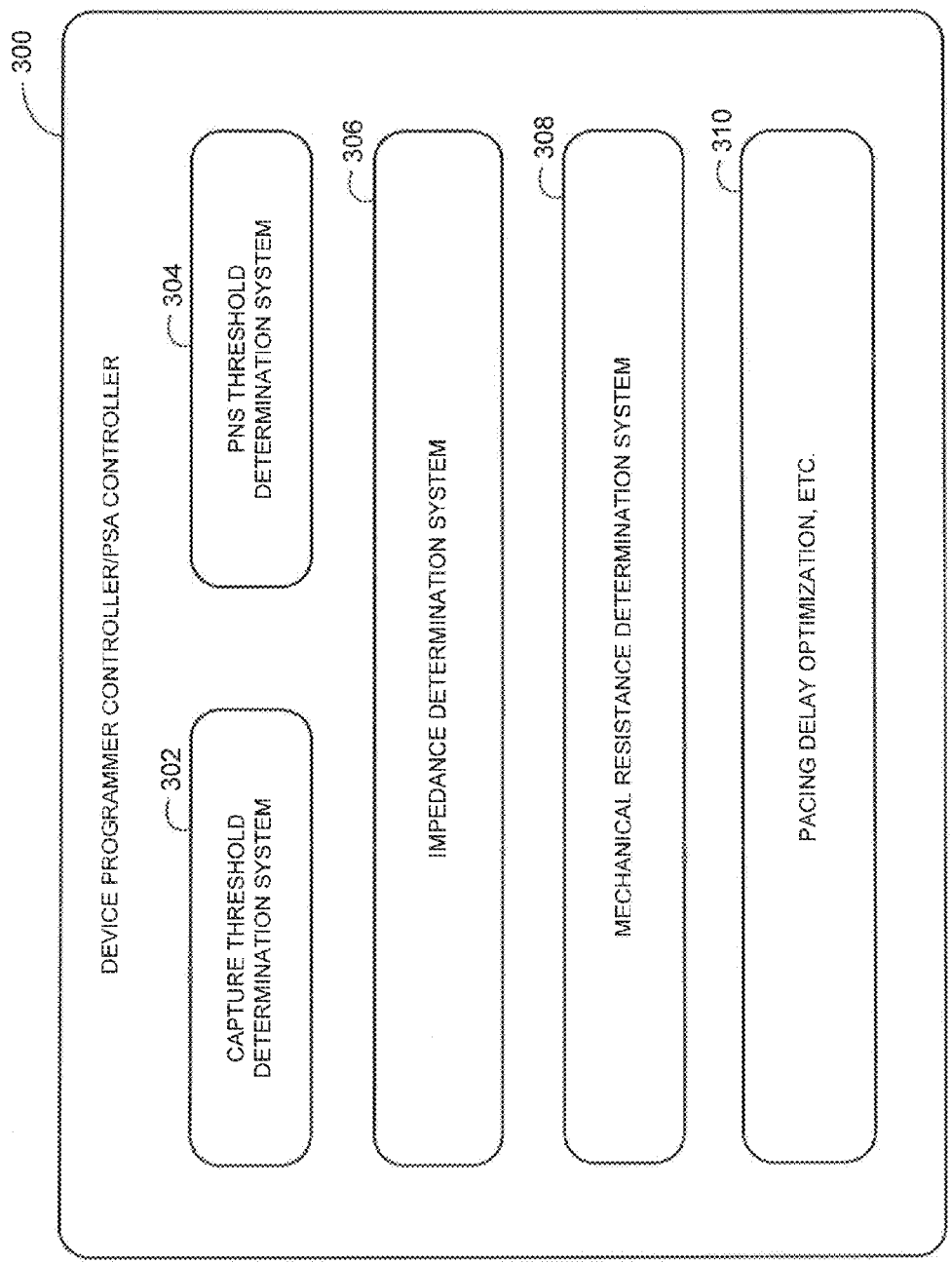
FIG. 6 is a block diagram illustrating pertinent components of a device programmer or PSA equipped to obtain implant location efficacy parameters for use with the exemplary technique of FIG. 3.

FIG. 6 illustrates pertinent components of a device programmer controller or PSA controller 300 for controlling or performing at least some of functions described above. Briefly, the system includes: a capture threshold determination system 302 operative to determine myocardial tissue capture thresholds and assess whether the PNS thresholds are too high; a PNS threshold determination system 304 operative to determine PNS thresholds and assess whether the PNS thresholds are too low; an impedance determination system 306 operative to measure electrical impedance of the lead; a mechanical resistance determination system 308 operative to measure mechanical resistance to lead insert and assess the presence of scar tissue at the site; and a pacing delay optimization system 310 operative to optimize pacing delays, etc or to perform or control other functions. Note that the figure is intended only to illustrate selected components, systems or sub-systems of the programmer/PSA that are pertinent to the functions described above and is not intended to show all of the features or components that might be provided. Also, depending upon the implementation, the various components of the controller may be implemented as separate software modules or the modules may be combined to permit a single module to perform multiple functions. In addition, some or all of these components may be implemented separately from the microcontroller, using application specific integrated circuits (ASICs) or the like.

Figure 7:
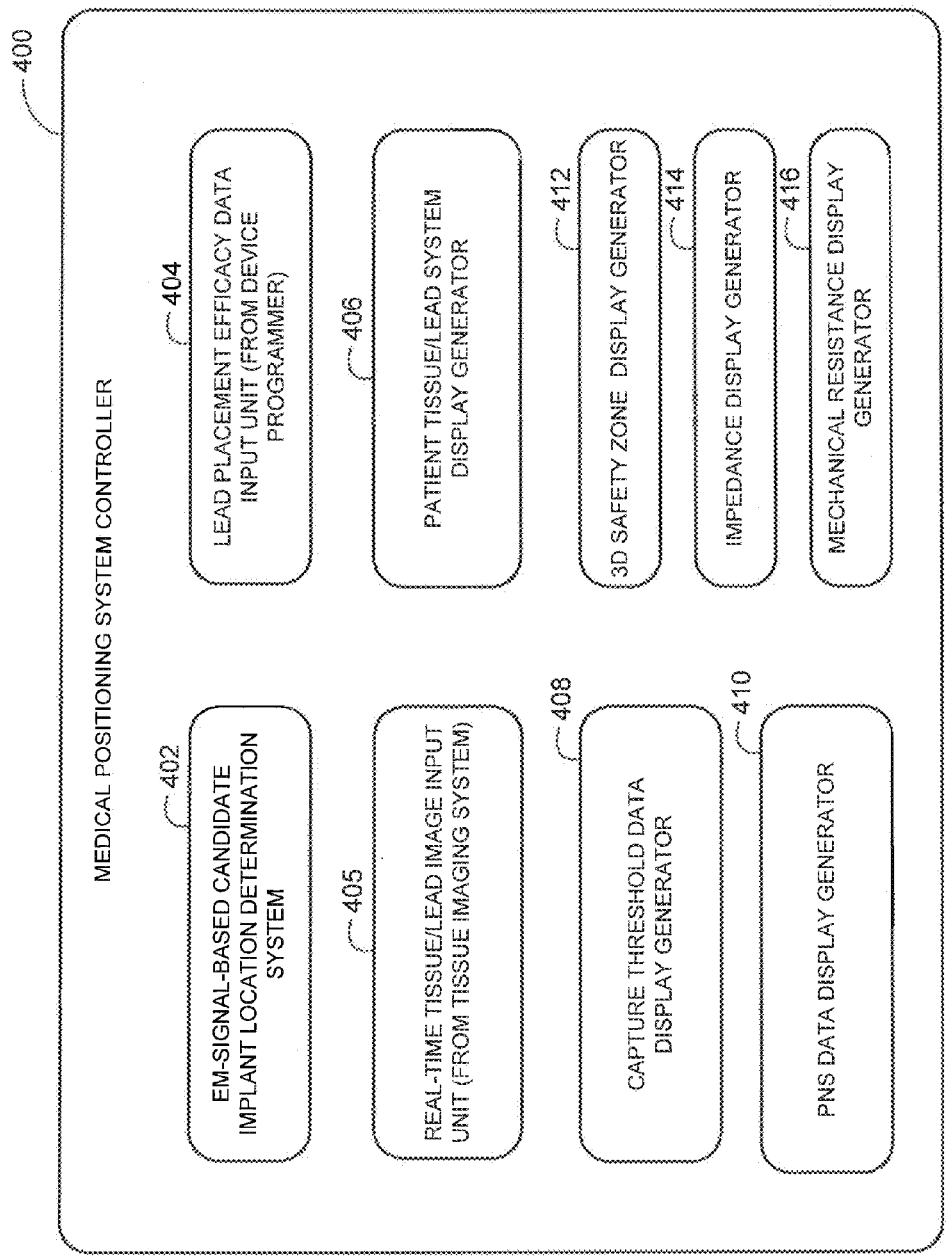
FIG. 7 is a block diagram illustrating pertinent components of an MPS equipped to obtain localization parameters for use in generating real-time displays in accordance with the exemplary technique of FIG. 3.

FIG. 7 illustrates pertinent components of an MPS controller 400 for controlling or performing at least some of functions described above. Briefly, the system includes: an electromagnetic signal-based candidate implant location determination system 402 operative to determine the location of a lead electrode to be implanted into patient tissue; a lead placement efficacy data input unit 404 operative to receive data from the device programmer specifying lead implant efficacy parameters such as capture thresholds, PNS thresholds, etc.; a real-time tissue/lead image input unit 405 operative to receive real-time or near real-time images from a tissue imaging system such as fluoroscope, ultrasonograph, CT device, etc.; and a patient tissue/lead system display generator 406 operative to generate displays of patient tissues and any lead systems or other medical devices implanted therein. The system also includes a capture threshold data display generator 408 operative to generate capture threshold icons or text markers for display at corresponding candidate implant locations; a PNS display generator 410 operative to generate PNS icons or text markers for display at corresponding candidate implant locations; a 3D safety zone display generator 412 operative to generate safety zone icons or text markers for display at corresponding candidate implant locations; an impedance display generator 414 operative to display icons or text markers pertaining to impedance for display at corresponding candidate implant locations (including, for example, an icon indicating if the impedance is found to be too high at the candidate location); and a mechanical resistance display generator 416 operative to display icons or text markers pertaining to torque or other parameters of mechanical resistance for display at corresponding candidate implant locations (including, for example, an icon indicating if excessive scar tissue is present. Note again that the figure is intended only to illustrate selected components, systems or sub-systems that are pertinent to the functions described above and is not intended to show all of the features or components that might be provided within an MPS system.

Figure 8:
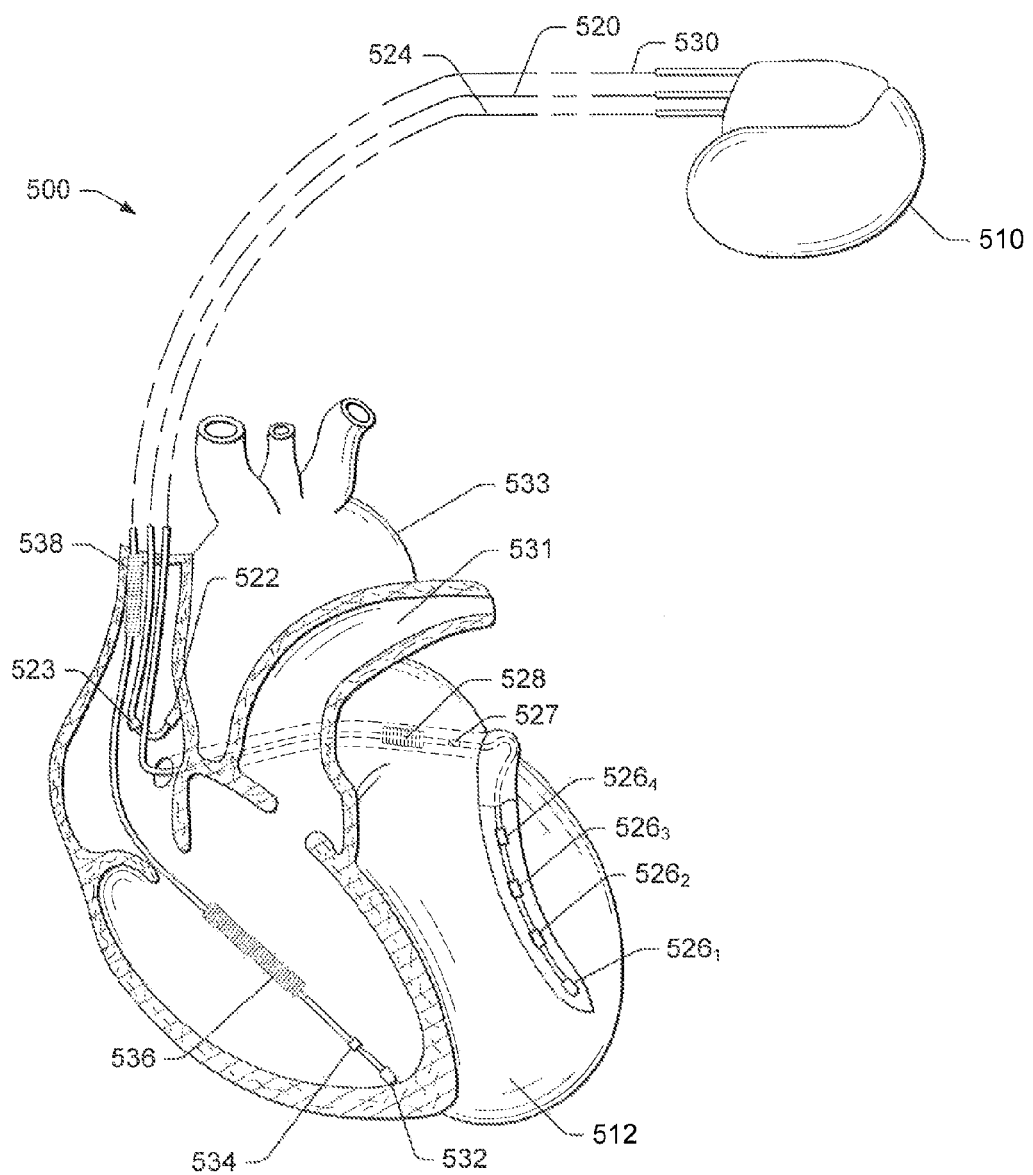
FIG. 8 is a simplified, partly cutaway view, illustrating an implantable medical device along with a set of leads implanted into the heart of the patient following completion of implant procedures.

For the sake of completeness, an exemplary CRMD lead system 500 (and corresponding CRMD 510) are illustrated in FIG. 8 after implant, showing various electrodes, coils, etc. More specifically, the figure provides a simplified block diagram of a CRMD 510, which is a dual-chamber stimulation device capable of treating both fast and slow arrhythmias with stimulation therapy, including cardioversion, defibrillation, and pacing stimulation, and may also be equipped to deliver CRT. To provide RA chamber pacing stimulation and sensing, CRMD 510 is shown in electrical communication with a heart 512 by way of a right atrial lead 520 having an atrial tip electrode 522 and an atrial ring electrode 523 implanted in the atrial appendage. CRMD 510 is also in electrical communication with the heart by way of a right ventricular lead 530 having, in this embodiment, a ventricular tip electrode 532, a right ventricular ring electrode 534, a right ventricular (RV) coil electrode 536, and a superior vena cave (SVC) coil electrode 538. Typically, the right ventricular lead 530 is transvenously inserted into the heart so as to place the RV coil electrode 536 in the right ventricular apex, and the SVC coil electrode 538 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, CRMD 510 is coupled to a multi-pole LV lead 524 designed for placement in the "CS region" via the CS os for positioning a distal electrode adjacent to the left ventricle and/or additional electrode(s) adjacent to the left atrium. As used herein, the phrase "CS region"

refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 524 is designed to receive atrial and ventricular cardiac signals and to deliver left ventricular pacing therapy using a set of four left ventricular electrodes $526_1$, $526_2$, $526_3$, and $526_4$, (thereby providing a quad-pole lead), left atrial pacing therapy using at least a left atrial ring electrode 527, and shocking therapy using at least a left atrial coil electrode 528. The $526_1$ LV electrode may also be referred to as a "tip" or "distal" LV electrode. The $526_4$ LV electrode may also be referred to as a "proximal" LV electrode. In other examples, more or fewer LV electrodes are provided. Although only three leads are shown in FIG. 8, it should be understood that additional leads (with one or more pacing, sensing and/or shocking electrodes) might be used and/or additional electrodes might be provided on the leads already shown, such as additional electrodes on the RV lead. It is also noted that, on present commercially-available hardware, there is often no separate electrode 527. That is, the electrode $526_4$ and the "left atrial ring electrode" 527 are the same. Both electrodes are shown for the sake of completeness and generality.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical lead system for implant within a patient, the method comprising:
    imaging tissues of the patient including at least a portion of a lead system being implanted;
    measuring at least one parameter representative of lead placement efficacy at at least a first and second candidate implant location within the tissues of the patient using a repositionable electrode of the lead system;
    measuring localization parameters identifying the candidate implant locations of the repositionable electrode within a three-dimensional coordinate system; and
    generating a display of images of the tissues of the patient and at least a portion of the lead system being implanted, the first candidate location of the repositionable electrode concurrently with the second candidate location of the repositionable electrode, and at least one parameter representative of lead placement efficacy at the candidate locations.

2. The method of claim 1 wherein at least a portion of the images are generated and displayed substantially in real-time.

3. The method of claim 1 wherein imaging the tissues of the patient including at least a portion of a lead system being implanted includes one or more of fluoroscopic imaging, computer aided tomography, ultrasonography, X-ray imaging, nuclear magnetic resonance (NMR) scanning; radioactive imaging; and thermography.

4. The method of claim 1 wherein the measuring at least one parameter representative of lead placement efficacy includes measuring one or more of a myocardial capture threshold, a phrenic nerve stimulation threshold, an electrical impedance between the repositionable electrode of the lead system and another electrode of the lead system, and a mechanical resistance.

5. The method of claim 4 wherein the lead is a screw-in lead and wherein mechanical resistance is determined by measuring a value representative of resistance to insertion of a tip of the lead into patient tissue.

6. The method of claim 5 further including comparing the mechanical resistance to a threshold indicative of scar tissue and generating a warning if the mechanical resistance exceeds the threshold.

7. The method of claim 1 wherein measuring at least one parameter representative of lead placement efficacy is performed by a medical device programmer system based on signals received from the lead system.

8. The method of claim 1 wherein measuring localization parameters identifying the candidate implant location of the repositionable electrode is performed by a medical positioning system (MPS).

9. The method of claim 8 wherein measuring localization parameters identifying the candidate implant locations is performed by the MPS using an electromagnetic field detector coupled to the lead near the repositionable electrode.

10. The method of claim 8 wherein generating the display is performed by the MPS based on images received from an imaging system.

11. The method of claim 1 wherein generating the display includes superimposing a graphical indication of at least one parameter representative of lead placement efficacy for at least one electrode of the lead system at, at least one, candidate implant location onto the images of the tissues of the patient.

12. The method of claim 11 wherein the graphical indication of at least one parameter representative of lead placement efficacy includes a textual indication of a myocardial capture threshold at the candidate implant locations.

13. The method of claim 11 wherein the graphical indication of at least one parameter representative of lead placement efficacy includes an indication of whether phrenic nerve stimulation would occur at the candidate implant locations using an electrical stimulation pulse delivered at, at least, the capture threshold.

14. The method of claim 11 wherein the graphical indication of at least one parameter representative of lead placement efficacy includes an indication of an electrical impedance measured between the electrode at the candidate implant locations and another selected electrode of the system.

15. The method of claim 11 wherein the graphical indication of at least one parameter representative of lead placement efficacy includes an indication of a mechanical resistance measured during insertion of the repositionable electrode into patient tissue at the candidate implant locations.

16. The method of claim 11 wherein the graphical indication of at least one parameter representative of lead placement efficacy includes an indication of whether a mechanical resistance measured during insertion of the repositionable electrode into patient tissue exceeds a predetermined scar tissue threshold.

17. The method of claim 11 wherein the graphical indication of at least one parameter representative of lead placement efficacy includes an indication of a safety distance surrounding the candidate implant locations specifying a minimum safe distance between candidate implant locations of the repositionable electrode.

18. The method of claim 11 wherein the graphical indication of at least one parameter representative of lead placement efficacy includes an indication of a safety distance surrounding the candidate implant location, wherein the safety distance indicates a minimum distance, determined in 3D, from the candidate implant location sufficient to substantially avoid adverse tissue perforation caused by closely spaced implant locations.

19. The method of claim 17 further including generating one or more of a visual or audible warning based on the safety distance.

20. The method of claim 11 wherein the graphical indication is generated based on predetermined thresholds whereby only sites deemed to be acceptable based on the thresholds are highlighted.

21. The method of claim 1 wherein generating the display includes generating a color-coded sensor icon having a color indicating the acceptability of implant parameters at a current location of the sensor icon.

22. The method of claim 1 further including receiving operator input for triggering a display of landmark icons representative of lead placement efficacy parameters at one or more candidate implant locations.

23. The method of claim 1 wherein the measuring at least one parameter representative of lead placement efficacy includes measuring one or more of a myocardial capture threshold, a phrenic nerve stimulation threshold, and a mechanical resistance to active fixation.

24. A system for use with an implantable medical lead system for implant in a patient, the system comprising:
   an imaging system operative to image tissues of the patient including at least a portion of a lead system being implanted;
   a lead placement efficacy parameter measurement system operative to measure at least one parameter representative of lead placement efficacy at at least a first and second candidate implant location within the tissues of the patient using a repositionable electrode of the lead system;
   a candidate implant location parameter measurement system operative to measure localization parameters identifying the candidate implant locations of the repositionable electrode within a three-dimensional coordinate system; and
   a candidate implant location display generator configured to generate a display of images of the tissues of the patient and at least a portion of the lead system being implanted, the first candidate location of the repositionable electrode concurrently with at least the second candidate location of the repositionable electrode, and at least one parameter representative of lead placement efficacy at the candidate locations.

25. The system of claim 24 wherein the lead placement efficacy parameter measurement system includes an implantable medical device programmer system.

26. The method of claim 24 wherein the candidate implant location parameter measurement system includes a medical positioning system (MPS).

27. A system for use with an implantable medical lead system for implant in a patient, the system comprising:
   means for imaging tissues of the patient including at least a portion of a lead system being implanted;
   means for measuring at least one parameter representative of lead placement efficacy at at least a first and second candidate implant location within the tissues of the patient using a repositionable electrode of the lead system;
   means for measuring localization parameters identifying the first and second candidate implant locations of the repositionable electrode within a three-dimensional coordinate system; and
   means for generating a display of images of the tissues of the patient and at least a portion of the lead system being implanted, the first candidate location of the repositionable electrode concurrently with at least the second candidate location of the repositionable electrode, and at least one parameter representative of lead placement efficacy at the candidate locations.

* * * * *